United States Patent
Okuda et al.

(10) Patent No.: US 8,920,169 B2
(45) Date of Patent: Dec. 30, 2014

(54) MOUTH OPENING INSTRUMENT AND METHOD

(71) Applicants: DENSO CORPORATION, Kariya, Aichi-pref. (JP); Kyushu University, National University Corporation, Fukuoka-shi, Fukuoka-pref. (JP)

(72) Inventors: Hideki Okuda, Nagoya (JP); Toshihiko Koyama, Anjo (JP); Tatsuya Ikegami, Nisshin (JP); Makoto Hashizume, Kasuga (JP); Riichi Ouchida, Fukuoka (JP); Kazutaka Toyoda, Kariya (JP); Byunghyun Cho, Fukuoka (JP)

(73) Assignees: DENSO CORPORATION, Kariya (JP); Kyushu University, National University Corporation, Fukuoka (JP)

( * ) Notice: Subject to any disclaimer, the term of this patent is extended or adjusted under 35 U.S.C. 154(b) by 0 days.

(21) Appl. No.: 13/909,164

(22) Filed: Jun. 4, 2013

(65) Prior Publication Data
US 2013/0323670 A1  Dec. 5, 2013

(30) Foreign Application Priority Data
Jun. 4, 2012 (JP) ................................. 2012-127057

(51) Int. Cl.
| | |
|---|---|
| A61C 1/08 | (2006.01) |
| A61C 5/00 | (2006.01) |
| A61C 19/04 | (2006.01) |
| A61C 5/14 | (2006.01) |
| A61B 1/24 | (2006.01) |
| A61B 19/00 | (2006.01) |

(52) U.S. Cl.
CPC ................ *A61C 5/007* (2013.01); *A61C 19/04* (2013.01); *A61C 5/14* (2013.01); *A61C 1/082* (2013.01); *A61B 1/24* (2013.01); *A61B 2019/5255* (2013.01)
USPC ......................................................... 433/140

(58) Field of Classification Search
CPC ....... A61C 5/14; A61B 1/24; A61B 2019/204
USPC ......................................................... 433/140
See application file for complete search history.

(56) References Cited

U.S. PATENT DOCUMENTS 4,700,695 A * 10/1987 Davis et al. ..................... 601/38
(Continued)

FOREIGN PATENT DOCUMENTS

| JP | 2007-282698 A | 11/2007 |
|---|---|---|
| JP | 4836081 B2 | 12/2011 |

*Primary Examiner* — Ralph Lewis
(74) *Attorney, Agent, or Firm* — Posz Law Group, PLC

(57) ABSTRACT

A mouth opening instrument includes an upper member suitable for attaching on an upper jaw side within the mouth of a patient and a lower member suitable for attaching on a lower jaw side. The instrument further includes a connecting section, a control section, and an input section. The connecting section connects end portions of the upper member and the lower member such that a resistance of opening or closing actions of the upper member and the lower member are controllable. The control section controls the resistance of opening or closing actions of the upper member and the lower member. The input section receives an operating state signal indicating an operating state of a dental treatment device. When the operating state signal indicating an operating state of a dental treatment device is inputted, the closing resistance of the upper member and the lower member is set to be greater than that at a time when the operating state signal is not inputted.

20 Claims, 7 Drawing Sheets

(56) References Cited

U.S. PATENT DOCUMENTS

| | | | |
|---|---|---|---|
| 4,883,046 A | * | 11/1989 | Fontenot .................... 601/38 |
| 4,991,566 A | * | 2/1991 | Shulman et al. ............ 600/213 |
| 5,462,435 A | * | 10/1995 | Young .......................... 433/140 |
| 2009/0253095 A1 | | 10/2009 | Salcedo et al. |
| 2013/0296654 A1 | * | 11/2013 | Olsen .......................... 600/205 |

* cited by examiner

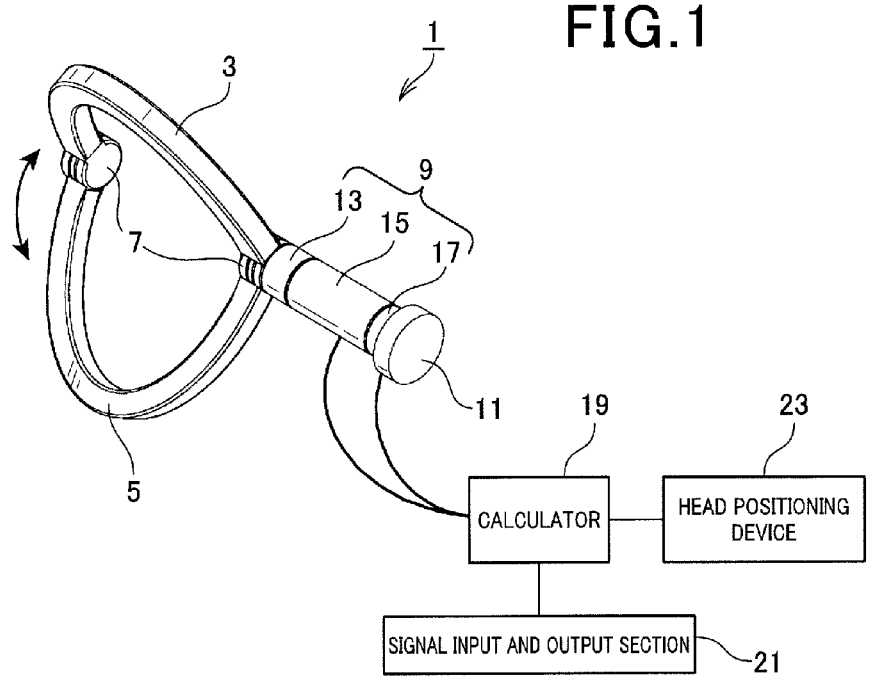
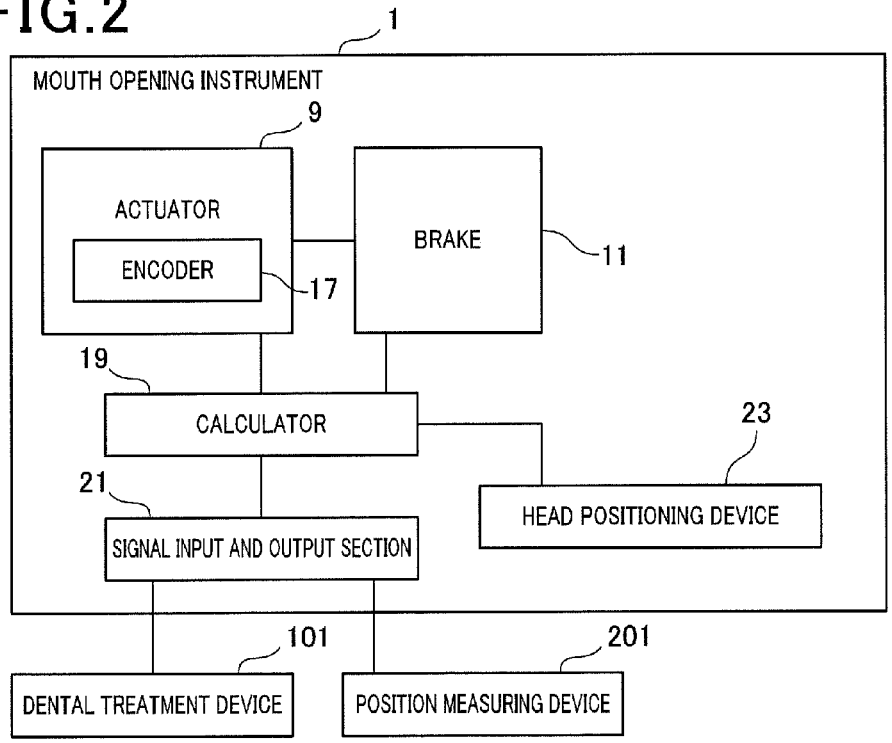

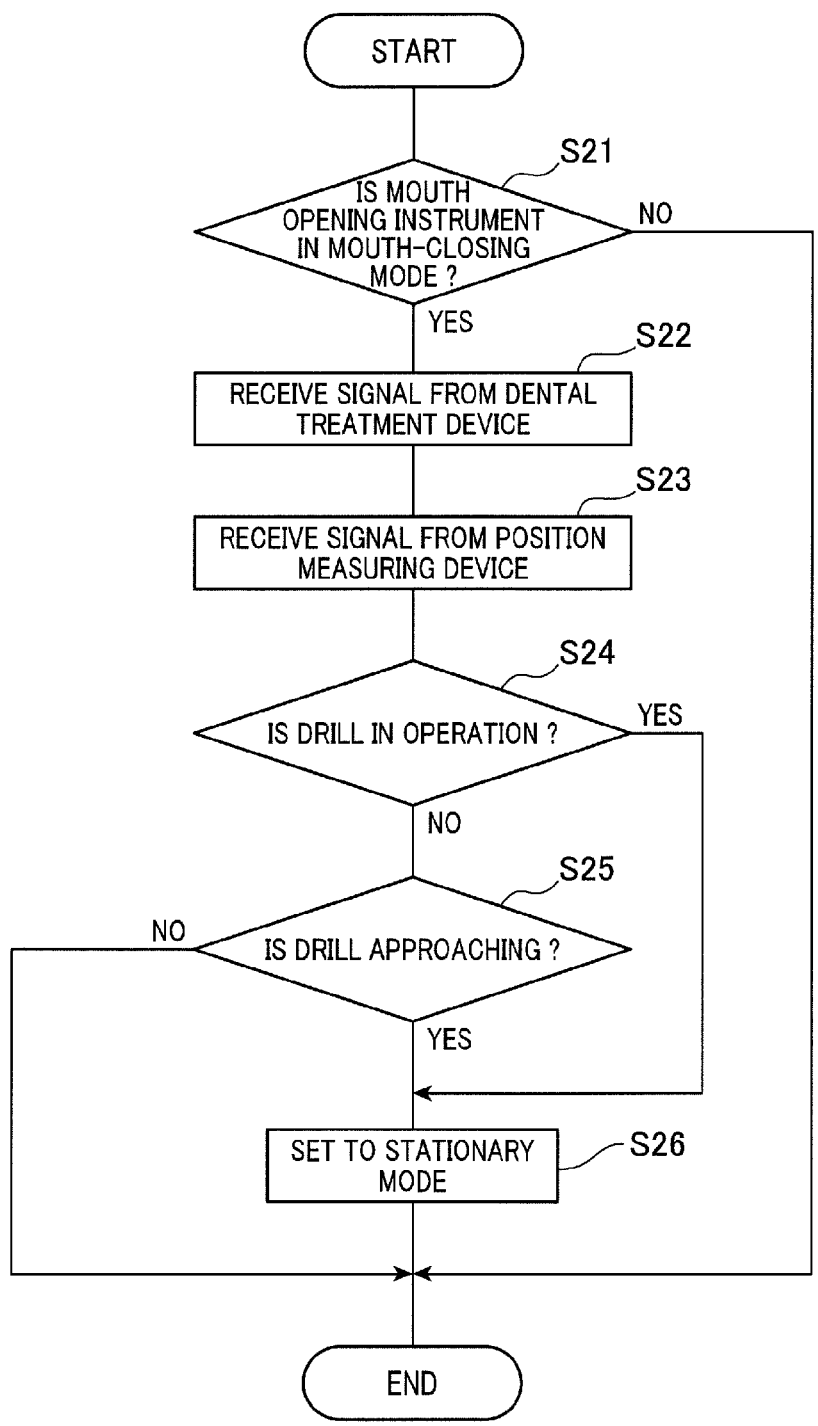

MOUTH OPENING INSTRUMENT AND METHOD

CROSS-REFERENCE TO RELATED APPLICATION

This application is based on and claims the benefit of priorities from earlier Japanese Patent Application No. 2012-127057 filed Jun. 4, 2012, the description of which is incorporated herein by reference.

BACKGROUND OF THE INVENTION

1. Technical Field

The present invention relates to a mouth opening instrument used, for example, in dental treatment.

2. Description of the Related Art

A patient's mouth is required to be kept open during dental treatment. Therefore, a mouth opening instrument that is set between the upper and lower teeth of the patient, such as that described in JP-A-2007-282698, is proposed.

When the mouth opening instrument described in JP-A-2007-282698 is used, the patient's mouth is kept open at all times regardless of the circumstances during the dental treatment. Therefore, the patient experiences distress, such as from not being able to swallow saliva. Thus, a mouth opening instrument is desired that can be appropriately controlled based on the circumstances during dental treatment.

SUMMARY

As an exemplary embodiment, the present application provides a mouth opening instrument including: an upper member suitable for attaching on an upper jaw side within the mouth of a patient; a lower member suitable for attaching on a lower jaw side; a connecting section that connects end portions of the upper member and the lower member such that a resistance of opening and/or closing actions of the upper member and the lower member is controllable; a control section that controls the resistance of opening and/or closing action of the upper member and the lower member; and an input section that receives an operating state signal indicating an operating state of a dental treatment device. When the certain operating state signal is inputted into the input section, the control section sets a closing resistance of the upper member and the lower member to be greater than that at a time when the certain operating state signal is not inputted.

In the mouth opening instrument according to the exemplary embodiment, when the certain operating state is inputted into the input section, the closing resistance of the upper member and the lower member is increased, making it difficult for the patient's mouth to close. Therefore, dental treatment can be appropriately performed. In addition, when the certain operating signal is not inputted into the input section, the closing resistance of the upper member and the lower member is reduced, and the patient's mouth can be easily closed. Therefore, distress experienced by the patient can be reduced.

BRIEF DESCRIPTION OF THE DRAWINGS

FIG. 1 is a configuration diagram of a mouth opening instrument;

FIG. 2 is a block diagram of an electrical circuit of the mouth opening instrument and a configuration diagram of a dental treatment system including the mouth opening instrument;

FIG. 3A and FIG. 3B are diagrams of a method of use of the mouth opening instrument, in which FIG. 3A is a side view and FIG. 3B is affront view;

FIG. 10 is a flowchart of processes performed by the mouth opening instrument.

DETAILED DESCRIPTION OF THE PREFERRED EMBODIMENTS

First Embodiment

A mouth opening instrument and a dental treatment system including the mouth opening instrument according to a first embodiment of the present invention will hereinafter be described with reference to FIG. 1 to FIG. 5.

[Configurations of the Mouth Opening Instrument and the Dental Treatment System]

Figure 3A:
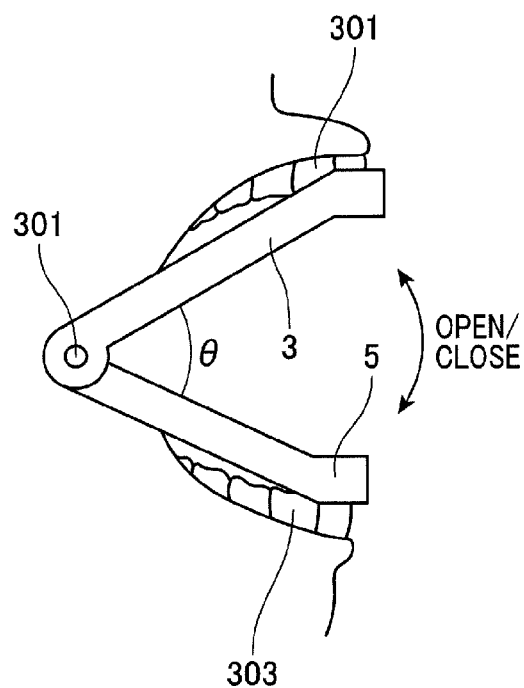
Figure 3B:
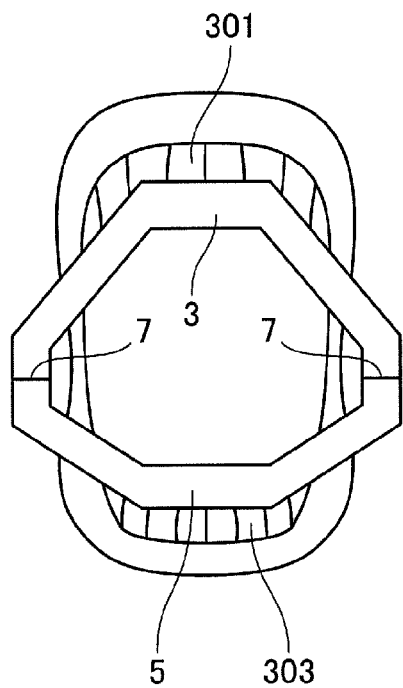

FIG. 1 is a configuration diagram of a mouth opening instrument 1 according to the first embodiment. FIG. 2 is a block diagram of an electrical circuit of the mouth opening instrument 1 and a configuration diagram of a dental treatment system including the mouth opening instrument 1. FIG. 3A and FIG. 3B are diagrams of a method of use of the mouth opening instrument 1, in which FIG. 3A is a side view and FIG. 3B is a front view.

As shown in FIG. 1, the mouth opening instrument 1 includes an actuator 9 that rotates an upper member 3 and a lower member 5. The actuator 9 is configured by a motor 15, an encoder 17, and a decelerator 13. Specifically, the rotational force of the motor 15 is decelerated by the decelerator 13 and transmitted to a connecting section 7. An opening angle θ formed by the upper member 3 and the lower member 5 (see FIG. 3A) is then increased or decreased. The encoder 17 detects the opening angle θ. The mouth opening instrument 1 includes a brake 11. The brake 11 provides a function for increasing force required when the mouth-opening operation and/or the mouth-closing operation is performed, or in other words, resistance (referred to, hereinafter, as resistance R) when the upper member 3 and the lower member 5 are rotated around the connecting section 7.

In the present embodiment, the upper member 3 and the lower member 5 are configured such that the resistance of opening and/or closing actions of the upper member 3 and the lower member 4 are controllable.

As shown in FIG. 3A and FIG. 3B, the mouth opening instrument includes the substantially U-shaped upper member 3, the substantially U-shaped lower member 5, and the connecting section 7. The upper member 3 comes into attach on the patient's teeth 301 on the upper jaw side. The lower member 5 comes into attachment with the patient's teeth 303 on the lower jaw side. The connecting section 7 connects the end portions of the upper member 3 and the lower member 5 by a pair of hinges such that the upper member 3 and the lower member 5 open and close.

FIG. 3A shows the mouth opening instrument 1 in which the upper member 3 and the lower member 5 rotate with the connecting section 7 as the center axis. However, the mouth opening instrument 1 may also be configured such that both ends of the upper member 3 and the lower member 5 slide in the up/down direction. For example, the connecting section 7 may be configured as a jack or the like that changes the distance between the upper member 3 and the lower member 5 while holding the direction of the lower member 5 in relation to the upper member 3 constant. Furthermore, the connecting section 7 may be configured such as to rotate the upper member 3 and the lower member 5 while sliding the upper member 3 and the lower member 5 in the up/down direction.

According to the first embodiment, "open and close" refers at least to an operation that changes the distance between the upper member 3 and the lower member 5, and includes "rotation." The distance from the connecting section 7 to the upper member 3 and the distance from the connecting section 7 to the lower member 5 may be constant or variable.

The actuator 9 and the brake 11 can control the resistance R when the patient's mouth is closing. In other words, the resistance R can be applied to the patient when the patient's mouth is closing as a result of the actuator 9 generating a driving force to open the mouth and the brake 11 being operated. When the driving force by the actuator 9 is large and the intensity of the brake 11 is increased, the overall resistance R is increased. Only one of either the actuator 9 or the brake 11 may control the resistance R.

In addition, as shown in FIG. 1 and FIG. 2, the mouth opening instrument 1 includes a calculator 19, a signal input and output section 21, and a head positioning device 23. The calculator 19 is configured by a known computer. The calculator 19 receives various signals from the actuator 9, the signal input and output section 21, and the like, and controls each section of the mouth opening instrument 1. In addition, a dental treatment device 101 and a position measuring device 201 are connected to the signal input and output section 21 of the mouth opening instrument 1. Signals are inputted and outputted between the signal input and output section 21 and the dental treatment device 101, and between the signal input and output section 21 and the position measuring device 201. This will be described in sequence, hereafter.

Signals received by the calculator 19 from the actuator 9 may indicate the magnitude of force in the direction reducing the opening angle θ (hereinafter referred to as "closing force") applied to the upper member 3 and the lower member 5. The actuator 9 can detect the closing force from a current value of the motor 15 required to hold the opening angle θ at a constant angle. In addition, other signals received by the calculator 19 from the actuator 9 may indicate the degree of the opening angle θ. As described above, the actuator 9 can detect the opening angle θ using the encoder 17.

Signals received by the calculator 19 from the signal input and output section 21 include a signal indicating ON (in-operation)/OFF (stopped) of the rotation of a drill 107, described hereafter, of the dental treatment device 101, a signal indicating the position of the drill 107, and a signal indicating the movement speed of the drill 107. These signals indicate the operating state of the dental treatment device 10.

The calculator 19 can set the mouth opening instrument 1 to any of mouth open mode, stationary mode, and mouth close mode. In mouth open mode, the actuator 9 performs a mouth-opening operation. In mouth open mode, the opening angle θ may be fixed. Alternatively, the resistance R may be increased from that in mouth close mode. In stationary mode, the actuator 9 and the brake 11 maintains the current opening angle θ.

In mouth close mode, the actuator 9 and the brake 11 are controlled to reduce the resistance R, and a mouth-closing operation can be performed by the force applied by the patient in an attempt to close his/her mouth. Setting of mouth open mode, stationary mode, and mouth close mode is performed by a signal being inputted into an inputting means (not shown). Details of a mode changing process will be described hereafter.

The calculator 19 also performs a withdrawing process, described hereafter. In the withdrawing process, when judged that the patient is attempting to close his mouth for whatever reason, the calculator 19 stops the rotation of the drill 107, moves the position of the drill 107 away from the patient's mouth, and withdraws the drill 107.

Figure 4:
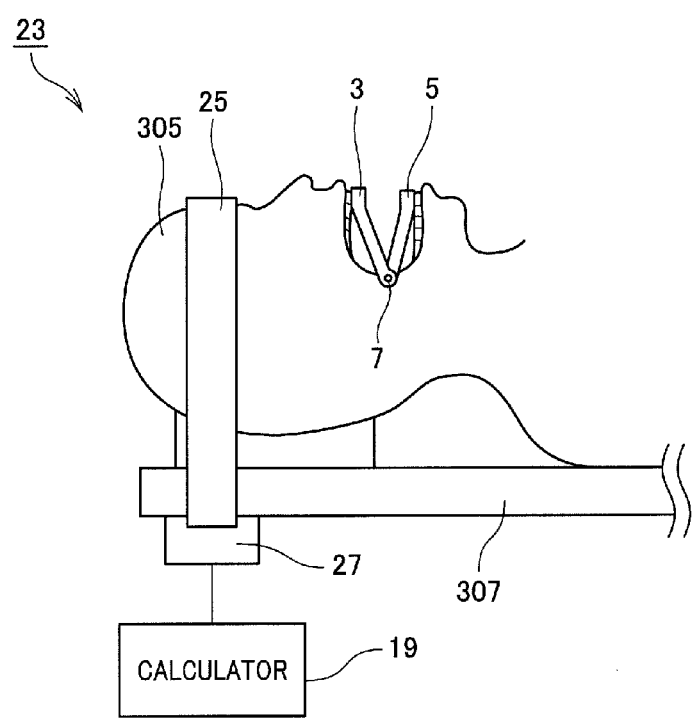
FIG. 4 is diagram of a configuration of a head positioning device.

Next, the head positioning device 23 will be described with reference to FIG. 4. FIG. 4 shows a configuration of the head positioning device 23. The head positioning device 23 includes a belt 25 and a tension adjusting section 27. The belt 25 is wrapped around the head 305 of the patient lying on a treatment table 307, and fixes the head 23 to the treatment table 307. The tension adjusting section 27 adjusts the tension of the belt 25. The tension adjusting section 27 decides the tension based on a signal received from the calculator 19. The head positioning device 23 increases the tension and firmly holds the head 305 stationary in stationary mode. The head positioning device 23 reduces the tension and allows motion and movement of the head 305 in mouth close mode.

Figure 5:
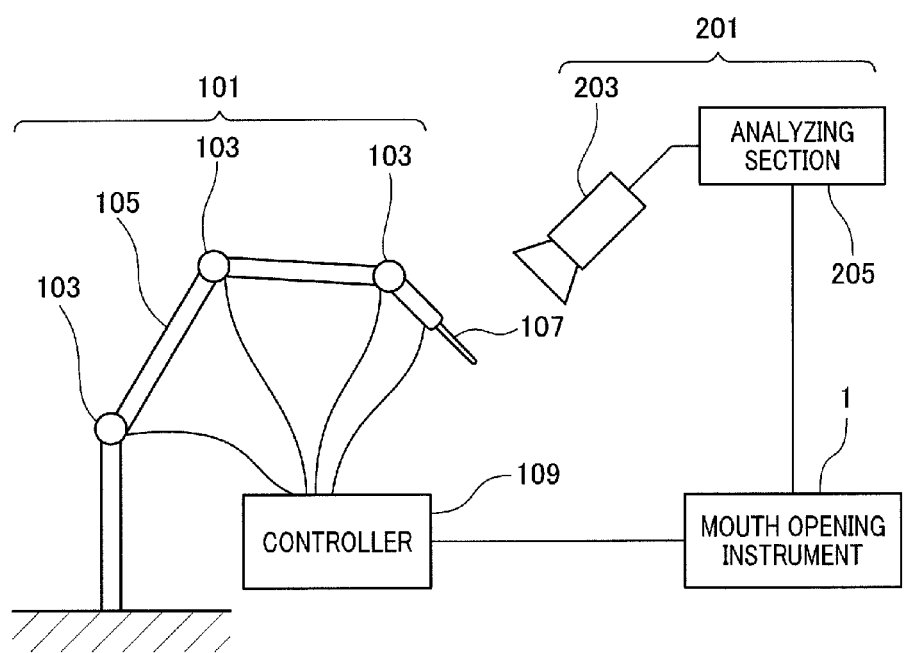
FIG. 5 is a diagram of configurations of a dental treatment device and a position measuring device.

Next, the dental treatment device 101 will be described with reference to FIG. 5. FIG. 5 is a diagram of the configurations of the dental treatment device 101 and the position measuring device 201. The dental treatment device 101 includes an arm 105, a dental treatment drill (referred to, hereinafter, as simply "drill") 107, and a controller 109. The arm 105 has a plurality of joints 103. The drill 107 is attached to the tip of the arm 105. The controller 109 controls the arm 105 and the drill 107. Each joint 103 includes a motor, an encoder, and a brake (not shown). The joints 103 perform predetermined flexing and rotation operations based on control signals from the controller 109, thereby controlling the direction and position of the drill 107. The controller 109 controls driving of the drill 107, or in other words, the ON/OFF of rotation, the rotation speed, and the like. The controller 109 is a known computer configured by a processor. The arm and the controller 109 are a known robot manipulator. The controller 109 periodically outputs a signal indicating ON/OFF of the rotation of the drill 107 to the mouth opening instrument 1. The signal indicating ON of the rotation of the drill 107 may be that indicating that the rotation of the drill 107 is currently ON. Alternatively, the signal may be that indicating that, although the rotation is currently OFF, the rotation will be turned ON after a predetermined amount of time.

The position measuring device 201 includes a camera 203 and an analyzing section 205. The camera 203 is used to capture an image of a field of view including the drill 107 being operated by a dentist. The analyzing section 205 calculates the position of the drill 107 (relative position in relation to any of the patient's mouth, the upper member 3, and the lower member 5) based on the image acquired by the camera 203. The position measuring device 201 periodically outputs a signal indicating the position of the drill 107 to the mouth opening instrument 1. In addition, the position measuring device 201 calculates a movement speed of the drill 107 from the position of the drill 107 at a certain time and the position of the drill 107 after the elapse of a predetermined amount of time. The position measuring device 201 periodically outputs a signal indicating the movement speed to the mouth opening instrument 1.

[Processes Performed by the Mouth Opening Instrument 1]

<Mode Changing Process>

Figure 6:
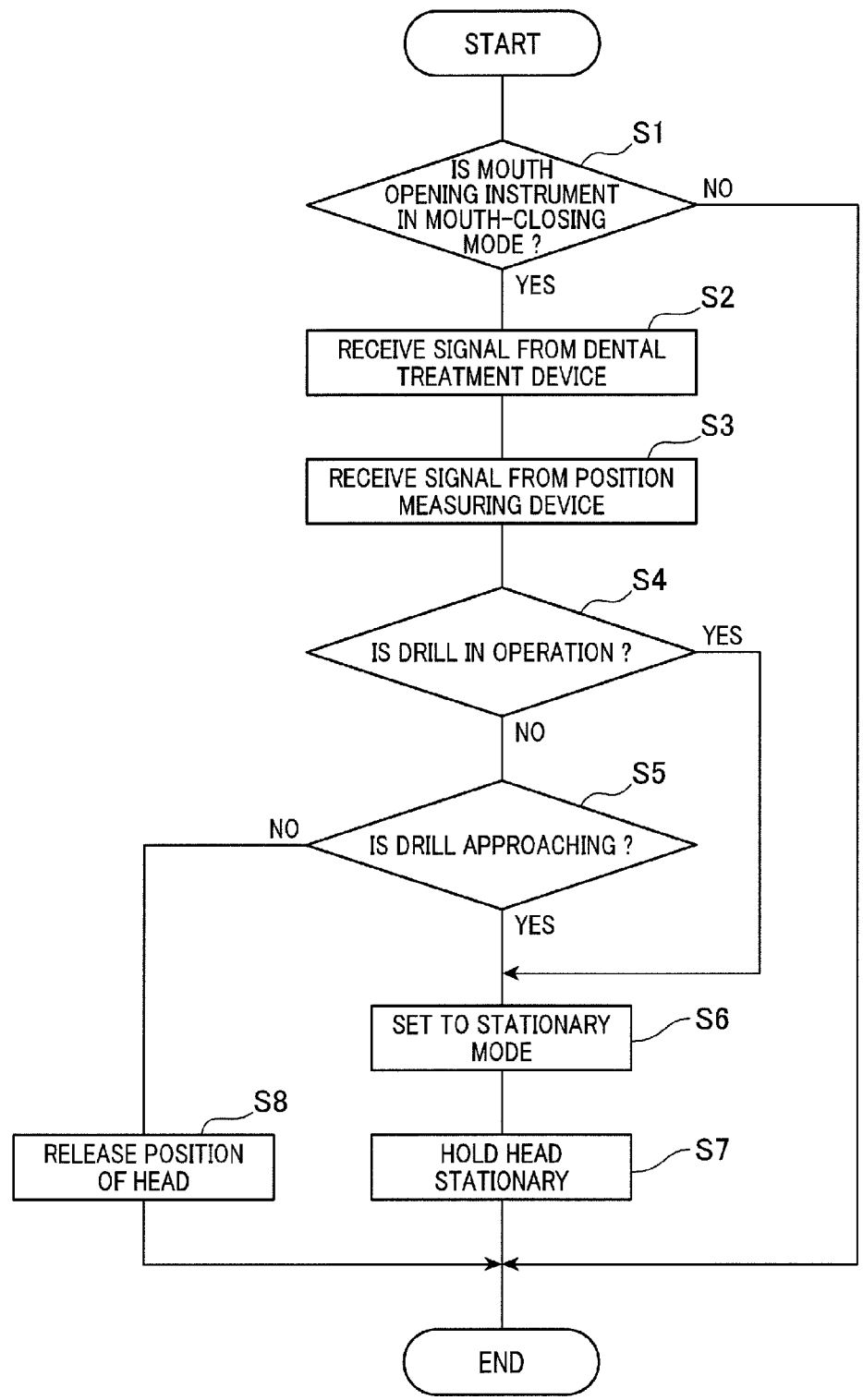
FIG. 6 is a flowchart of processes performed by the mouth opening instrument.

The mode changing process performed by the calculator 19 of the mouth opening instrument 1 will be described with reference to the flowchart in FIG. 6. The process is repeatedly performed at a predetermined interval.

At Step 1, the calculator 19 judges the mode to which the mouth opening instrument 1 is set. When judged that the mouth opening instrument 1 is in mouth close mode, the calculator 19 proceeds to Step 2. When judged that the mouth opening instrument 1 is in stationary mode or mouth open mode, the calculator 19 ends the mode changing process. At Step 2, the calculator 19 acquires a signal outputted from the dental treatment device 101 and received by the signal input and output section 21. The signal indicates ON/OFF of the rotation of the drill 107.

At Step 3, the calculator 19 acquires a signal outputted from the position measuring device 201 and received by the signal input and output section 21. The signal indicates the position of the drill 107. At Step 4, the calculator 19 judges whether or not the signal acquired at Step 2 is a signal indicating that the rotation of the drill 107 is ON. When judged that the signal indicates that the rotation of the drill 107 is ON, the calculator 19 proceeds to Step 6. When judged otherwise, the calculator 19 proceeds to Step 5. The signal indicating that the rotation of the drill 107 is ON may be a signal with an output of zero (the input signal is zero).

At Step 5, the calculator 19 judges whether or not a distance from the position of the drill 107 identified by the signal acquired at Step 3 to the patient's mouth is a predetermined threshold value or less. When judged that the distance is the predetermined threshold value or less, the calculator 19 proceeds to Step 6. When judged that the distance is greater than the predetermined threshold value, the calculator 19 proceeds to Step 8. The signal indicating that the distance to the patient's mouth is the predetermined threshold value or less may be a signal with an output of zero (the input signal is zero).

At Step 6, the calculator 19 changes the mode of the mouth opening instrument 1 to stationary mode. In other words, the calculator 19 sets the resistance R to be greater than the current resistance R in mouth close mode. At Step 7, the calculator 19 controls the tension adjusting section 27. As a result, the tension of the belt 25 (the magnitude of the force holding the patient's head 305 stationary) is increased, and the head 305 is firmly fixed to the treatment table 307.

On the other hand, when judged NO at Step 5, the calculator 19 proceeds to Step 8 and reduces the tension of the belt 25. When the tension is already relaxed, the calculator 19 performs no particular processing operation. Then, the calculator 19 ends the mode changing process with the mouth opening instrument 1 remaining in mouth close mode.

<Withdrawing Process>

Figure 7:
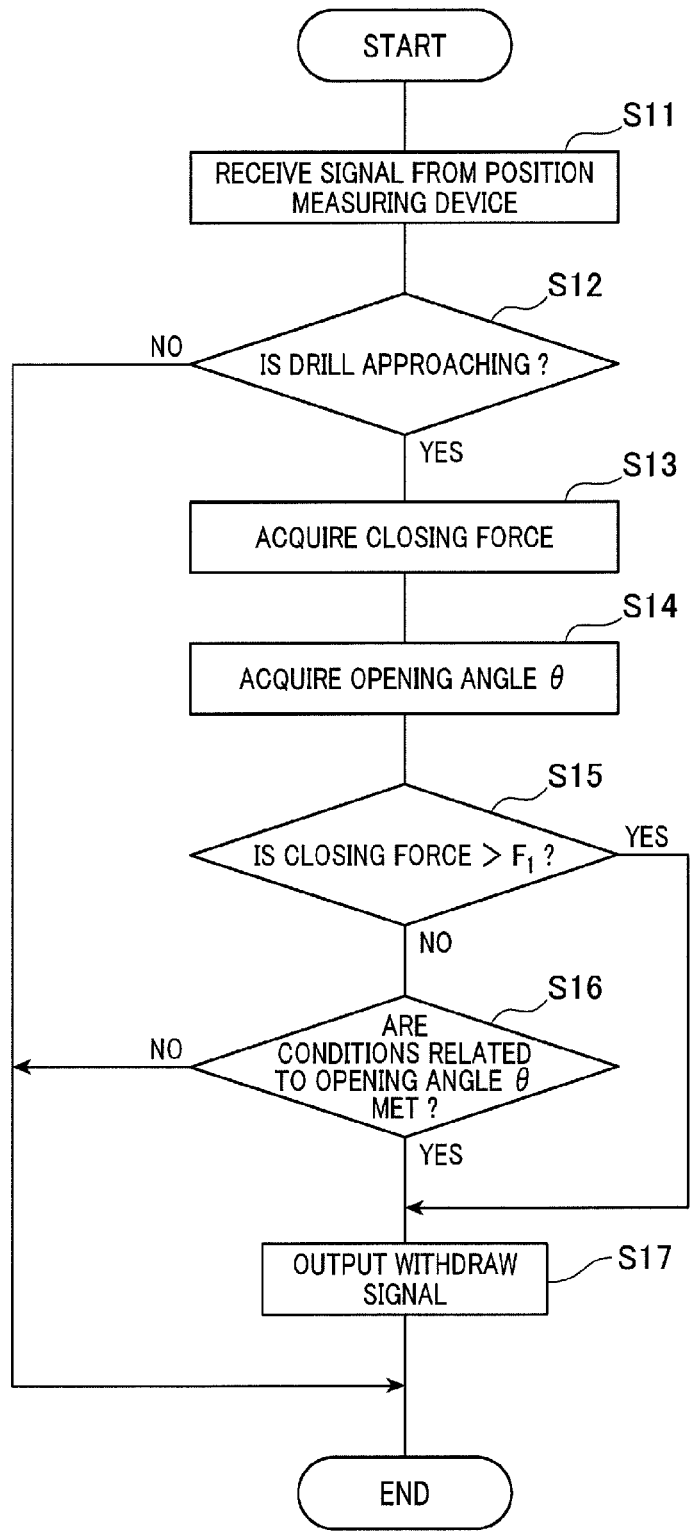
FIG. 7 is a flowchart of processes performed by the mouth opening instrument.

The withdrawing process performed by the calculator 19 of the mouth opening instrument 1 will be described with reference to the flowchart in FIG. 7. The process is repeatedly performed at a predetermined interval.

At Step 11, the calculator 19 acquires a signal outputted from the position measuring device 201 and received by the signal input and output section 21. The signal indicates the position of the drill 107. At Step 12, the calculator 19 judges whether or not a distance from the position of the drill 107 identified by the signal acquired at Step 11 to the patient's mouth is a predetermined threshold value or less. When judged that the distance is the predetermined threshold value or less, the calculator 19 proceeds to Step 13. When the distance is greater than the threshold value, the calculator 19 ends the withdrawing process.

At Step 13, the calculator 19 acquires the closing force from the actuator 9. At Step 14, the calculator 19 acquires the opening angle θ from the actuator 19. At Step 15, the calculator 19 judges whether or not the closing force acquired at Step 13 is greater than a predetermined threshold value $F_1$. When judged that the closing force is greater than the threshold value $F_1$, the calculator 19 proceeds to Step 17. When judged that the closing force is the threshold value $F_1$ or less, the calculator 19 proceeds to Step 16.

At Step 16, the calculator 19 judges whether or not the opening angle θ acquired at Step 14 meets the following conditions X and Y:

condition X: the opening angle θ is less than a predetermined threshold value $F_2$ condition Y: with the most recent opening angle as θn, when the opening angle at a predetermined amount of time ΔT before the most recent opening angle θn is θp, θn is smaller than θp (in other words, the opening angle θ has decreased), and the absolute value of the difference between θn and θp (the amount of decrease in the opening angle θ) is greater than a predetermined threshold value $F_3$.

When judged that even either of condition X and condition Y is met, the calculator 19 proceeds to Step 17. When judged that neither of condition X and condition Y is met, the calculator 19 ends the withdrawing process. At Step 17, the calculator 19 outputs a signal unique to the instance at Step 17 to the dental treatment device 101 via the signal input and output section 21. The calculator 19 then ends the withdrawing process. Upon receiving the unique signal, the dental treatment device 101 stops the rotation of the drill 107, moves the position of the drill 107 away from the patient's mouth, and withdraws the drill 107. The process performed by the dental treatment device 101 when the unique signal is received may be only one of either stopping the rotation of the drill 107 or withdrawing the drill 107.

[Effects Achieved by the Mouth Opening Instrument 1]

(1) When the signal indicating that the rotation of the drill 107 is ON is received from the dental treatment device 101 or when a signal indicating that the drill 107 is approaching the patient's mouth is received from the position measuring device 201, the mouth opening instrument 1 is switched to stationary mode and increases the resistance R, making it difficult for the patient's mouth to close. Therefore, dental treatment can be appropriately performed. In addition, in other instances, the mouth opening instrument 1 is kept in mouth close mode (mode in which the resistance R is smaller than that in stationary mode) and the patient's mouth can be easily closed. Therefore, distress experienced by the patient can be reduced.

(2) When set to stationary mode, the mouth opening instrument 1 increases the tension in the belt 25 of the head positioning device 23, and can firmly fix the patient's head 305 to the treatment table 307. As a result, reduction in treatment accuracy caused by movement of the patient's head during treatment can be suppressed.

(3) When the closing force, or in other words, the force applied by the patient in an attempt to close his mouth is strong, or when the opening angle θ is decreasing, the mouth opening instrument 1 withdraws the drill 107 from the patient's mouth. As a result, unnecessary contact between the drill 107 and the tissue within the patient's mouth can be prevented. Safety during treatment can be ensured.

Variation Examples (1) In the mode changing process, judgment regarding ON/OFF of the rotation of the drill 107 (Step 4) and judgment regarding the position of the drill 107 (Step 5) are both performed. However, only one of either may be performed. For example, when judged NO at Step 4, the calculator 19 may proceed to Step 8 without performing the processing operation at Step 5. Alternatively, the calculator 19 may proceed to Step 5 after Step 3 without performing the judgment at Step 4.

(2) The mouth opening instrument 1 may not include the head positioning device 23. In this instance, in the mode changing process, the processing operations at Step 7 and Step 8 are unnecessary.

(3) In the withdrawing process, judgment regarding the magnitude of closing force (Step 15) and judgment regarding whether the conditions regarding the opening angle θ are satisfied (Step 16) are both performed. However, only one of either may be performed. For example, when judged no at Step 15, the calculator 19 may end the withdrawing process without performing the processing operation at Step 16. Alternatively, the calculator 19 may proceed to Step 16 after Step 14 without performing the judgment at Step 15. Furthermore, at Step 16, the calculator 19 may judge whether or not the condition is met regarding only either of the conditions X and Y. The calculator 19 may then proceed to Step 17 when judged that the condition is met. When judged that the condition is not met, the calculator 19 may end the withdrawing process.

(4) Instead of the optical position measuring device 201, the position of the drill 107 may be detected using a magnetic or mechanical position measuring device, and the position information may be outputted to the mouth opening instrument 1. In addition, the position of the drill 107 may be detected from the state of the arm 105 (flexing direction, flexing amount, rotation direction, and rotation amount of the joints 103) included in the dental treatment device 101, and the position information may be outputted to the mouth opening instrument 1.

(5) A shape-memory alloy may be used as the actuator 9. In this instance, the opening angle θ can be changed by the temperature of the shape-memory alloy being controlled.

(6) The head positioning device 23 may hold the patient's head 305 stationary using a member other than the belt 25 (such as a pair of plate-shaped members sandwiching the patient's head 305 from both sides, a plurality of bar-shaped members disposed around the patient's head 305, or the like).

(7) In the mode changing process, in the processing operation at Step 4, the calculator 19 may judge whether or not the movement speed of the drill 107 is a predetermined value or more. When judged that the movement speed is the predetermined value or more, the calculator 19 may proceed to Step 6. When judged that the movement speed is less than the predetermined value, the calculator 19 may proceed to Step 5. Alternatively, in the processing operation at Step 5, the calculator 19 may judge whether or not the movement speed of the drill 107 is a predetermined value or more. When judged that the movement speed is the predetermined value or more, the calculator 19 may proceed to Step 6. When judged that the movement speed is less than the predetermined value, the calculator 19 may proceed to Step 8. Alternatively, a step may be added between Step 4 and Step 5 to judge whether or not the movement speed of the drill 107 is a predetermined value or more. When judged that the movement speed is the predetermined value or more, the calculator 19 may proceed to Step 6. When judged that the movement speed is less than the predetermined value, the calculator 19 may proceed to Step 5. The movement speed of the drill 107 can be calculated from the movement amount between the position of the drill 107 acquired at Step 3 performed most recently, and the position of the drill 107 acquired at Step 3 performed a predetermined amount of time earlier. Moreover, a signal indicating the movement speed of the drill 107 may be received from the position measuring device 201.

Second Embodiment

A mouth opening instrument according to a second embodiment of the present invention will hereinafter be described.

[Configuration of the Mouth Opening Instrument]

Figure 8:
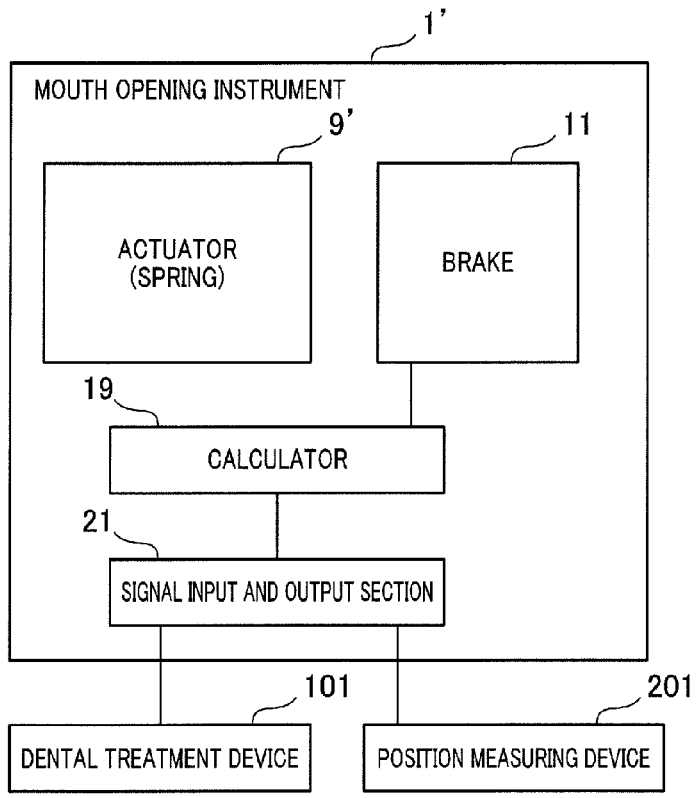
FIG. 8 is a block diagram of an electrical configuration of the mouth opening instrument.
Figure 9:
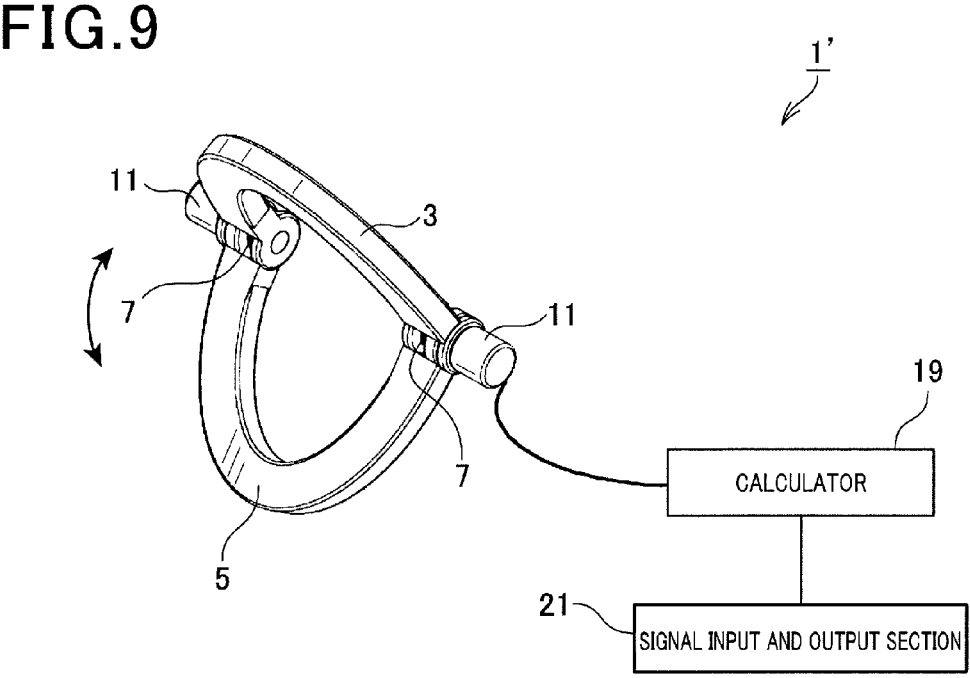
FIG. 9 is a diagram of another configuration of the mouth opening instrument.

A configuration of a mouth opening instrument 1' according to a second embodiment will be described with reference to FIG. 8 and FIG. 9. In FIG. 8 and FIG. 9, components that are similar to those according to the first embodiment are given the same reference numbers. The configuration of the mouth opening instrument 1' is similar to that of the mouth opening instrument 1 according to the first embodiment. However, the mouth opening instrument 1' differs in that the head positioning device 23 according to the first embodiment is not included, and the structure of an actuator 9 according to the second embodiment differs from that of the actuator 9 according to the first embodiment. The mouth opening instrument 1' will be described mainly focusing on the differences. Descriptions regarding sections similar to those according to the first embodiment are omitted or simplified.

The mouth opening instrument 1' includes the upper member 3, the lower member 5, the connecting section 7, the actuator 9', the brake 11, the calculator 19, and the signal input and output section 21. The actuator 9' is configured by an elastic member (spring) that urges against the upper member 3 and the lower member 5 in a direction increasing the opening angle θ, with a constant force at all times. The brake 11 provides a function for controlling the resistance R. In other words, the resistance R during the mouth-closing operation is applied when the brake 11 is operated.

The calculator 19 receives various signals from the signal input and output section 21 and the like, and controls each section of the mouth opening instrument 1'. Signals received from the signal input and output section 21 include a signal indicating ON/OFF of the rotation of the drill 107 of the dental treatment device 101, and a signal indicating the position of the drill 107.

The calculator 19 can set the mouth opening instrument 1' to either of stationary mode and non-stationary mode. In stationary mode, the resistance R is increased by the brake 11 and the current opening angle θ is maintained. In non-stationary mode, the brake 11 is released and the resistance R becomes smaller than that in stationary mode. In non-stationary mode, when a closing force greater than the elastic force of the actuator 9' is applied to the upper member 3 and the lower member 5, the mouth-closing operation is performed. On the other hand, when the closing force is smaller than the elastic force of the actuator 9, the mouth-opening operation is performed until the opening angle θ reaches a predetermined upper limit value. Setting of stationary mode and non-stationary mode is performed by a signal being inputted into an inputting means (not shown). In addition, the mode is changed by a mode changing process, described hereafter. The configurations of the signal input and output section 21, the dental treatment device 101, and the position measuring device 201 are similar to those according to the first embodiment.

[Mode Changing Process Performed by the Mouth Opening Instrument 1']

The mode changing process performed by the calculator 19 of the mouth opening instrument 1' will be described with reference to the flowchart in FIG. 10. The process is repeatedly performed at a predetermined interval.

At Step 21, the calculator 19 judges the mode to which the mouth opening instrument 1' is set. When judged that the mouth opening instrument 1' is in non-stationary mode, the calculator 19 proceeds to Step 22. When judged that the mouth opening instrument 1' is in stationary mode, the calculator 19 ends the mode changing process. At Step 22, the calculator 19 acquires a signal outputted from the dental treatment device 101 and received by the signal input and output section 21. The signal indicates ON/OFF of the rotation of the drill 107.

At Step 23, the calculator 19 acquires a signal outputted from the position measuring device 201 and received by the signal input and output section 21. The signal indicates the position of the drill 107. At Step 24, the calculator 19 judges whether or not the signal acquired at Step 22 is a signal indicating that the rotation of the drill 107 is ON. When judged that the signal indicates that the rotation of the drill 107 is ON, the calculator 19 proceeds to Step 26. When judged otherwise, the calculator 19 proceeds to Step 25.

At Step 25, the calculator 19 judges whether or not the distance from the position of the drill 107 identified by the signal acquired at Step 23 to the patient's mouth is a predetermined threshold value or less. When judged that the distance is the predetermined threshold value or less, the calculator 19 proceeds to Step 26. When judged that the distance is greater than the threshold value, the calculator 19 ends the mode changing process.

At Step 26, the calculator 19 changes the mode of the mouth opening instrument 1' to stationary mode. In other words, the calculator 19 sets the resistance R to be greater than the current resistance R in non-stationary mode. The calculator 19 then ends the mode changing process.

[Effects Achieved by the Mouth Opening Instrument 1']

When the signal indicating that the rotation of the drill 107 is ON is received from the dental treatment device 101 or when a signal indicating that the drill 107 is approaching the patient's mouth is received from the position measuring device 201, the mouth opening instrument 1 is switched to stationary mode and increases the resistance R, making it difficult for the patient's mouth to close. Therefore, dental treatment can be appropriately performed. In addition, in other instances, the mouth opening instrument 1 is kept in non-stationary mode (mode in which the resistance R is smaller than that in stationary mode) and the patient's mouth can be easily closed. Therefore, distress experienced by the patient can be reduced.

Variation Examples (1) In the mode changing process, judgment regarding ON/OFF of the rotation of the drill 107 (Step 24) and judgment regarding the position of the drill 107 (Step 25) are both performed. However, only one of either may be performed. For example, when judged NO at Step 24, the calculator 19 may end the mode changing process without performing the processing operation at Step 25. Alternatively, the calculator 19 may proceed to Step 25 after Step 23 without performing the judgment at Step 24.

(2) The mouth opening instrument 1' may include the head positioning device 23. In this instance, a processing operation for increasing the tension of the belt 25 of the head positioning device 23 can be performed before or after Step 26.

(3) Instead of a spring, a shape-memory alloy may be used as the actuator 9'. In this instance, the opening angle θ can be changed by the temperature of the shape-memory alloy being controlled.

(4) An elastic member (such as rubber) other than a spring may be used as the actuator 9'.

(5) The mouth opening instrument 1' may include a sensor for detecting closing force of the upper member and the lower member or a sensor for detecting the opening angle θ. A withdrawing process similar to that according to the first embodiment may be performed.

(6) In the mode changing process, in the processing operation at Step 24, the calculator 19 may judge whether or not the movement speed of the drill 107 is a predetermined value or more. When judged that the movement speed is the predetermined value or more, the calculator 19 may proceed to Step 26. When judged that the movement speed is less than the predetermined value, the calculator 19 may proceed to Step 25. Alternatively, in the processing operation at Step 25, the calculator 19 may judge whether or not the movement speed of the drill 107 is a predetermined value or more. When judged that the movement speed is the predetermined value or more, the calculator 19 may proceed to Step 26. When judged that the movement speed is less than the predetermined value, the calculator 19 may end the mode changing process. Alternatively, a step may be added between Step 24 and Step 25 to judge whether or not the movement speed of the drill 107 is a predetermined value or more. When judged that the movement speed is the predetermined value or more, the calculator 19 may proceed to Step 26. When judged that the movement speed is less than the predetermined value, the calculator 19 may proceed to Step 25. The movement speed of the drill 107 can be calculated from the movement amount between the position of the drill 107 acquired at Step 3 performed most recently, and the position of the drill 107 acquired at Step 3 performed a predetermined amount of time earlier. Moreover, a signal indicating the movement speed of the drill 107 may be received from the position measuring device 201.

In the foregoing embodiments and variation examples, the actuator 9 (or 9') and the brake 11 are an example of "a control section that controls a resistance of opening and/or closing action of the upper member and the lower member". The calculator 19 and the signal input and output section 21 are an example of "a first signal output section" and a "second signal output section". The signal input and output section 21 is an example of "an input section that receives an operating state signal indicating an operating state of a dental treatment device". The actuator 9 and 9' are each an example of "a mouth-closing force detecting section". The encoder 17 that detects the opening angle θ is an example of "a mouth-opening amount detecting section". The head positioning device 23 is an example of "a head positioning section".

In addition, the dental treatment drill 107 is an example of "a dental treatment tool included in the dental treatment device". "A signal indicating that the rotation of the drill 107 is ON" and "a signal, among the signals acquired at Step 3, indicating that the distance to the patient's mouth is the predetermined threshold value or less" are each an example of "a certain operating state signal". "A signal indicating ON (in operation) or OFF (stopped) of rotation of a drill 107 in a dental treatment device 101", "a signal indicating a position of the drill 107" and "a signal indicating a moving speed of the drill 107" are each an example of "an operation state signal indicating an operation state of the dental treatment device". "Mouth-opening angle θ" is an example of "an amount of mouth-opening".

What is claimed is:

1. A mouth opening instrument, comprising:
an upper member configured to be attached on an upper jaw side within a mouth of a patient;
a lower member configured to be attached on a lower jaw side within the mouth of the patient;
a connecting section mutually connecting end portions of both the upper member and the lower member and permitting relative movement of distal portions of the upper and lower members respectively toward and away from each other that respectively corresponds to an opening or a closing of the upper and lower members and to a closing action or an opening action of the patient's mouth;
an input section configured to receive operating state signals indicating an operating state of a dental treatment device, the operating state signals including a designated operating state signal;
a control section comprising a brake arranged with the connection section and upper and lower members, the brake passively generating a resistance to the opening or closing of the upper and lower members, and the control section being configured to receive the operating signals from the input section and to control an amount of the resistance to the opening or closing of the upper and lower members; and
wherein the control section receives the designated operating state signal from the input device and sets the resistance of the brake to the closing of the upper and lower members to a resistance greater than a resistance for closing the upper and lower members when the designated operating state signal is not received.

2. The mouth opening instrument according to claim 1, wherein the designated operating state signal indicates one of
i) a state in which a dental treatment tool provided in the dental treatment device is in operation,
ii) a state in which a distance between the tool and the patient's mouth is within a predetermined value, and
iii) a state in which the dental treatment tool is moving at a speed over a predetermined value.

3. The mouth opening instrument according to claim 2, further comprising:
a mouth-closing force detecting section that detects a closing force exerted between the upper member and the lower member, the closing force being a force applied to the upper and lower members during the closing of the upper and lower members; and
a first signal output section that outputs a first signal to a device outside the mouth opening instrument when the closing force detected by the mouth-closing force detecting section is equal to or more than a predetermined threshold.

4. The mouth opening instrument according to claim 3, further comprising:
a mouth-opening amount detecting section that detects an opened amount of the patient's mouth; and
a second signal output section that outputs a second signal to a device outside the mouth opening instrument when the opened amount of the patient's mouth detected by the mouth-opening amount detecting section is equal to or less than a predetermined threshold or when a decrease in the opened amount of the patient's mouth is equal to or more than a predetermined threshold.

5. The mouth opening instrument according to claim 4, further comprising:
a head positioning section that holds a head of the patient, wherein when the input section receives the designated operating state signal, the head positioning section sets a force for holding the patient's head that is greater than a force for holding the patient's head provided when the input section does not receive the designated operating state signal.

6. The mouth opening instrument according to claim 3, further comprising:
a head positioning section that holds a head of the patient, wherein when the input section receives the designated operating state signal, the head positioning section sets a force for holding the patient's head to a force that is greater than the force for holding the patient's head provided when the input section does not receive the designated operating state signal.

7. The mouth opening instrument according to claim 2, further comprising:
a mouth-opening amount detecting section that detects an opened amount of the patient's mouth; and
a second signal output section that outputs a second signal to a device outside the mouth opening instrument when the amount of the opening of the patient's mouth detected by the mouth-opening amount detecting section is equal to or less than a predetermined threshold or when a decrease in the opened amount of the patient's mouth is equal to or more than a predetermined threshold.

8. The mouth opening instrument according to claim 2, further comprising:
a head positioning section that holds a head of the patient, wherein when the input section receives the designated operating state signal, the head positioning section sets a force for holding the patient's head to a force that is greater than a force for holding the patient's head provided when the input section does not receive the designated operating state signal.

9. The mouth opening instrument according to claim 1, further comprising:
a mouth-closing force detecting section that detects a closing force exerted between the upper member and the lower member, the closing force being a force applied to the upper and lower members during the closing of the upper and lower members; and
a first signal output section that outputs a first signal to a device outside the mouth opening instrument when the closing force detected by the mouth-closing force detecting section is equal to or more than a predetermined threshold.

10. The mouth opening instrument according to claim 9, wherein the first signal is a signal indicating stoppage in rotation of a drill of the dental treatment device or movement of the drill away from the patient's mouth.

11. The mouth opening instrument according to claim 1, further comprising:
a mouth-opening amount detecting section that detects an opened amount of the patient's mouth; and
a second signal output section that outputs a second signal to a device outside the mouth opening instrument when the opened amount of the patient's mouth detected by the mouth-opening amount detecting section is equal to or less than a predetermined threshold or when a decrease in the opened amount of the patient's mouth is equal to or more than a predetermined threshold.

12. The mouth opening instrument according to claim 11, wherein the second signal is a signal indicating stoppage in rotation of a drill of the dental treatment device or movement of the drill away from the patient's mouth.

13. The mouth opening instrument according to claim 1, further comprising:
a head positioning section that holds a head of the patient, wherein when the input section receives the designated operating state signal, the head positioning section sets a force for holding the patient's head that is greater than a force for holding the patient's head provided when the input section does not receive the designated operating state signal.

14. A method for controlling a mouth opening instrument, wherein the mouth opening instrument includes:
an upper member configured to be attached on an upper jaw side within a mouth of a patient;
a lower member configured to be attached on a lower jaw side within the mouth of the patient;
a connecting section mutually connecting end portions of both the upper member and the lower member and permitting relative movement of distal portions of the upper and lower members respectively toward and away from each other that respectively correspond to an opening or a closing of the upper and lower members and to a closing action or an opening action of the patient's mouth; and
a control section comprising a brake arranged with the connection section and upper and lower members, the brake being configured to passively generate a resistance to the opening or closing of the upper and lower members, and the control section being configured to receive the operating signals from the input section and to control an amount of the resistance to the opening or closing of the upper and lower members,
the method comprising steps of:
receiving an operating state signal indicating an operating state of a dental treatment device, the operating state signal including a designated operating state signal;
determining whether the received operating signal is a designated operating state signal;
after determining that the received operating signal is the designated operating state signal, setting the resistance of the closing of the upper and lower members to a resistance greater than a resistance of the closing of the upper and lower members when the designated operating state signal is not received.

15. The method according to claim 14, wherein the designated operating state signal indicates one of
i) a state in which a dental treatment tool included provided in the dental treatment device is in operation,
ii) a state in which a distance between the tool and the patient's mouth is within a predetermined value, and
iii) a state in which the tool is moved at a speed over a predetermined value.

16. The method according to claim 15, further comprising:
detecting a closing force exerted between the upper member and the lower member, the closing force being a force applied to the upper and lower members during the closing of the upper and lower members; and
outputting a first signal outside the mouth opening instrument when the closing force is equal to or more than a predetermined threshold.

17. The method according to claim 16, wherein the first signal is a signal indicating stoppage in rotation of a drill of the dental treatment device or movement of the drill away from the patient's mouth.

18. The method according to claim 15, further comprising:
detecting an amount of opening of the patient's mouth; and
outputting a second signal outside the mouth opening instrument when the opened amount of the patient's mouth is equal to or less than a predetermined threshold or when a decrease in the opened amount of the patient's mouth is equal to or more than a predetermined threshold.

19. The method according to claim 18, wherein the second signal is a signal indicating stoppage in rotation of a drill of the dental treatment device or movement of the drill away from the patient's mouth.

20. The method according to claim 15, further comprising:
when the designated operating state signal is received, setting a force for holding a head of the patient to a force greater than a force for holding the patient's head provided when the designated operating state signal is not received.

* * * * *